(12) United States Patent
Orszulak et al.

(10) Patent No.: US 8,475,447 B2
(45) Date of Patent: *Jul. 2, 2013

(54) SYSTEM AND METHOD FOR CLOSED LOOP MONITORING OF MONOPOLAR ELECTROSURGICAL APPARATUS

(75) Inventors: James H. Orszulak, Nederland, CO (US); Robert H. Wham, Boulder, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/592,523

(22) Filed: Aug. 23, 2012

(65) Prior Publication Data

US 2012/0316555 A1    Dec. 13, 2012

Related U.S. Application Data

(63) Continuation of application No. 13/074,769, filed on Mar. 29, 2011, now Pat. No. 8,267,928, which is a continuation of application No. 11/657,174, filed on Jan. 24, 2007, now Pat. No. 7,927,328.

(60) Provisional application No. 60/761,440, filed on Jan. 24, 2006.

(51) Int. Cl.
*A61B 18/18* (2006.01)

(52) U.S. Cl.
USPC .................................. 606/34; 606/32; 606/37

(58) Field of Classification Search
USPC ......................................... 606/32–35, 37–40
See application file for complete search history.

(56) References Cited

U.S. PATENT DOCUMENTS

| | | | |
|---|---|---|---|
| 1,787,709 | A | 1/1931 | Wappler |
| 1,813,902 | A | 7/1931 | Bovie |
| 1,841,968 | A | 1/1932 | Lowry |
| 1,863,118 | A | 6/1932 | Liebel |
| 1,945,867 | A | 2/1934 | Rawls |
| 2,693,106 | A | 6/1951 | Henry |
| 2,827,056 | A | 3/1958 | Degelman |
| 2,849,611 | A | 8/1958 | Adams |

(Continued)

FOREIGN PATENT DOCUMENTS

| DE | 179607 | 3/1905 |
|---|---|---|
| DE | 1099658 | 2/1961 |

(Continued)

OTHER PUBLICATIONS

U.S. Appl. No. 10/406,690, filed Apr. 3, 2003, Robert J. Behnke, II.

(Continued)

*Primary Examiner* — Linda Dvorak
*Assistant Examiner* — Amanda Scott

(57) ABSTRACT

An electrosurgical system is disclosed comprising a generator configured to electrosurgical coagulation waveforms. The generator includes a closed loop control system for controlling the electrosurgical coagulation waveforms. The closed loop control system includes a sensor configured to sense a tissue property and/or an energy property and to transmit the tissue property and/or the energy property as one or more sensor signals having an amplitude. The control system also includes a gain controller configured to process the at least one sensor signal to reduce the amplitude of the sensor signals and to obtain a signal to noise ratio of the at sensor signals within a predetermine range. A microprocessor coupled to the generator and is configured to adjust the electrosurgical coagulation waveforms as a function of the sensor signals.

18 Claims, 2 Drawing Sheets

U.S. PATENT DOCUMENTS

| | | |
|---|---|---|
| 2,883,198 A | 4/1959 | Narumi |
| 3,001,132 A | 9/1961 | Britt |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,247,815 A | 1/1981 | Larsen et al. |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |

| | | | | | |
|---|---|---|---|---|---|
| 4,767,999 A | 8/1988 | VerPlanck | 5,334,183 A | 8/1994 | Wuchinich |
| 4,768,969 A | 9/1988 | Bauer et al. | 5,334,193 A | 8/1994 | Nardella |
| 4,785,829 A | 11/1988 | Convert et al. | 5,341,807 A | 8/1994 | Nardella |
| 4,788,634 A | 11/1988 | Schlecht et al. | 5,342,356 A | 8/1994 | Ellman |
| 4,805,621 A | 2/1989 | Heinze et al. | 5,342,357 A | 8/1994 | Nardella |
| 4,818,954 A | 4/1989 | Flachenecker et al. | 5,342,409 A | 8/1994 | Mullett |
| 4,827,927 A | 5/1989 | Newton | 5,346,406 A | 9/1994 | Hoffman et al. |
| 4,848,335 A | 7/1989 | Manes | 5,346,491 A | 9/1994 | Oertli |
| 4,860,745 A | 8/1989 | Farin et al. | 5,348,554 A | 9/1994 | Imran et al. |
| 4,862,889 A | 9/1989 | Feucht | 5,354,325 A | 10/1994 | Chive et al. |
| 4,887,199 A | 12/1989 | Whittle | 5,364,392 A | 11/1994 | Warner et al. |
| 4,890,610 A | 1/1990 | Kirwan et al. | 5,369,567 A | 11/1994 | Furuta et al. |
| 4,903,696 A | 2/1990 | Stasz et al. | 5,370,645 A | 12/1994 | Klicek et al. |
| 4,907,589 A | 3/1990 | Cosman | 5,370,672 A | 12/1994 | Fowler et al. |
| 4,922,210 A | 5/1990 | Flachenecker et al. | 5,370,675 A | 12/1994 | Edwards et al. |
| 4,925,089 A | 5/1990 | Chaparro et al. | 5,372,596 A | 12/1994 | Klicek et al. |
| 4,931,047 A | 6/1990 | Broadwin et al. | 5,383,874 A | 1/1995 | Jackson |
| 4,931,717 A | 6/1990 | Gray et al. | 5,383,876 A | 1/1995 | Nardella |
| 4,938,761 A | 7/1990 | Ensslin | 5,383,917 A | 1/1995 | Desai et al. |
| 4,942,313 A | 7/1990 | Kinzel | 5,385,148 A | 1/1995 | Lesh et al. |
| 4,959,606 A | 9/1990 | Forge | 5,396,194 A | 3/1995 | Williamson et al. |
| 4,961,047 A | 10/1990 | Carder | 5,400,267 A | 3/1995 | Denen et al. |
| 4,961,435 A | 10/1990 | Kitagawa et al. | 5,403,311 A | 4/1995 | Abele et al. |
| 4,966,597 A | 10/1990 | Cosman | 5,403,312 A | 4/1995 | Yates et al. |
| 4,969,885 A | 11/1990 | Farin | 5,409,000 A | 4/1995 | Imran |
| 4,992,719 A | 2/1991 | Harvey | 5,409,485 A | 4/1995 | Suda |
| 4,993,430 A | 2/1991 | Shimoyama et al. | 5,413,573 A | 5/1995 | Koivukangas |
| 4,995,877 A | 2/1991 | Ams et al. | 5,414,238 A | 5/1995 | Steigerwald et al. |
| 5,015,227 A | 5/1991 | Broadwin et al. | 5,417,719 A | 5/1995 | Hull et al. |
| 5,024,668 A | 6/1991 | Peters et al. | 5,422,567 A | 6/1995 | Matsunaga |
| 5,044,977 A | 9/1991 | Vindigni | 5,422,926 A | 6/1995 | Smith et al. |
| 5,057,105 A | 10/1991 | Malone et al. | 5,423,808 A | 6/1995 | Edwards et al. |
| 5,067,953 A | 11/1991 | Feucht | 5,423,809 A | 6/1995 | Klicek |
| 5,075,839 A | 12/1991 | Fisher et al. | 5,423,810 A | 6/1995 | Goble et al. |
| 5,078,153 A | 1/1992 | Nordlander et al. | 5,423,811 A | 6/1995 | Imran et al. |
| 5,087,257 A | 2/1992 | Farin | 5,425,704 A | 6/1995 | Sakurai et al. |
| 5,099,840 A | 3/1992 | Goble et al. | 5,429,596 A | 7/1995 | Arias et al. |
| 5,103,804 A | 4/1992 | Abele et al. | 5,430,434 A | 7/1995 | Lederer et al. |
| 5,108,389 A | 4/1992 | Cosmescu | 5,432,459 A | 7/1995 | Thompson |
| 5,108,391 A | 4/1992 | Flachenecker | 5,433,739 A | 7/1995 | Sluijter et al. |
| 5,113,116 A | 5/1992 | Wilson | 5,436,566 A | 7/1995 | Thompson |
| 5,119,284 A | 6/1992 | Fisher et al. | 5,438,302 A | 8/1995 | Goble |
| 5,122,137 A | 6/1992 | Lennox | 5,443,462 A | 8/1995 | Hannant |
| 5,133,711 A | 7/1992 | Hagen | 5,443,463 A | 8/1995 | Stern et al. |
| 5,151,102 A | 9/1992 | Kamiyama et al. | 5,445,635 A | 8/1995 | Denen |
| 5,152,762 A | 10/1992 | McElhenney | 5,445,638 A | 8/1995 | Rydell et al. |
| 5,157,603 A | 10/1992 | Scheller et al. | 5,448,466 A | 9/1995 | Erckert |
| 5,160,334 A | 11/1992 | Billings et al. | 5,451,224 A | 9/1995 | Goble et al. |
| 5,161,893 A | 11/1992 | Shigezawa et al. | 5,452,725 A | 9/1995 | Martenson |
| 5,167,658 A | 12/1992 | Ensslin | 5,454,809 A | 10/1995 | Janssen |
| 5,167,659 A | 12/1992 | Ohtomo et al. | 5,458,597 A | 10/1995 | Edwards et al. |
| 5,190,517 A | 3/1993 | Zieve et al. | 5,462,521 A | 10/1995 | Brucker et al. |
| 5,196,008 A | 3/1993 | Kuenecke | 5,472,441 A | 12/1995 | Edwards et al. |
| 5,196,009 A | 3/1993 | Kirwan, Jr. | 5,472,443 A | 12/1995 | Cordis et al. |
| 5,201,900 A | 4/1993 | Nardella | 5,474,464 A | 12/1995 | Drewnicki |
| 5,207,691 A | 5/1993 | Nardella | 5,480,399 A | 1/1996 | Hebborn |
| 5,216,338 A | 6/1993 | Wilson | 5,483,952 A | 1/1996 | Aranyi |
| 5,230,623 A | 7/1993 | Guthrie et al. | 5,496,312 A | 3/1996 | Klicek |
| 5,233,515 A | 8/1993 | Cosman | 5,496,313 A | 3/1996 | Gentelia et al. |
| 5,234,427 A | 8/1993 | Ohtomo et al. | 5,496,314 A | 3/1996 | Eggers |
| 5,244,462 A | 9/1993 | Delahuerga et al. | 5,498,261 A | 3/1996 | Strul |
| 5,249,121 A | 9/1993 | Baum et al. | 5,500,012 A | 3/1996 | Brucker et al. |
| 5,249,585 A | 10/1993 | Turner et al. | 5,500,616 A | 3/1996 | Ochi |
| 5,254,117 A | 10/1993 | Rigby et al. | 5,511,993 A | 4/1996 | Yamada et al. |
| RE34,432 E | 11/1993 | Bertrand | 5,514,129 A | 5/1996 | Smith |
| 5,267,994 A | 12/1993 | Gentelia et al. | 5,520,684 A | 5/1996 | Imran |
| 5,267,997 A | 12/1993 | Farin | 5,531,774 A | 7/1996 | Schulman et al. |
| 5,271,413 A | 12/1993 | Dalamagas et al. | 5,534,018 A | 7/1996 | Wahlstrand et al. |
| 5,281,213 A | 1/1994 | Milder et al. | 5,536,267 A | 7/1996 | Edwards et al. |
| 5,282,840 A | 2/1994 | Hudrlik | 5,540,677 A | 7/1996 | Sinofsky |
| 5,290,283 A | 3/1994 | Suda | 5,540,681 A | 7/1996 | Strul et al. |
| 5,295,857 A | 3/1994 | Toly | 5,540,682 A | 7/1996 | Gardner et al. |
| 5,300,068 A | 4/1994 | Rosar et al. | 5,540,683 A | 7/1996 | Ichikawa |
| 5,300,070 A | 4/1994 | Gentelia | 5,540,684 A | 7/1996 | Hassler, Jr. |
| 5,304,917 A | 4/1994 | Somerville | 5,541,376 A | 7/1996 | Ladtkow et al. |
| 5,318,563 A | 6/1994 | Malis et al. | 5,545,161 A | 8/1996 | Imran |
| 5,323,778 A | 6/1994 | Kandarpa et al. | 5,556,396 A | 9/1996 | Cohen et al. |
| 5,324,283 A | 6/1994 | Heckele | 5,558,671 A | 9/1996 | Yates |
| 5,330,518 A | 7/1994 | Neilson et al. | 5,559,688 A | 9/1996 | Pringle |

| | | | | | |
|---|---|---|---|---|---|
| 5,562,720 A | 10/1996 | Stern et al. | 5,843,075 A | 12/1998 | Taylor |
| 5,569,242 A | 10/1996 | Lax et al. | 5,846,236 A | 12/1998 | Lindenmeier et al. |
| 5,571,147 A | 11/1996 | Sluijter et al. | 5,849,010 A | 12/1998 | Wurzer et al. |
| 5,573,533 A | 11/1996 | Strul | 5,853,409 A | 12/1998 | Swanson et al. |
| 5,584,830 A | 12/1996 | Ladd et al. | 5,860,832 A | 1/1999 | Wayt et al. |
| 5,588,432 A | 12/1996 | Crowley | 5,865,788 A | 2/1999 | Edwards et al. |
| 5,596,466 A | 1/1997 | Ochi | 5,868,737 A | 2/1999 | Taylor et al. |
| 5,596,995 A | 1/1997 | Sherman et al. | 5,868,739 A | 2/1999 | Lindenmeier et al. |
| 5,599,344 A | 2/1997 | Paterson | 5,868,740 A | 2/1999 | LeVeen et al. |
| 5,599,345 A | 2/1997 | Edwards et al. | 5,871,481 A | 2/1999 | Kannenberg et al. |
| 5,599,348 A | 2/1997 | Gentelia et al. | 5,891,142 A | 4/1999 | Eggers et al. |
| 5,605,150 A | 2/1997 | Radons et al. | 5,893,848 A | 4/1999 | Negus et al. |
| 5,609,560 A | 3/1997 | Ichikawa et al. | 5,897,552 A | 4/1999 | Edwards et al. |
| 5,613,966 A | 3/1997 | Makower et al. | 5,906,614 A | 5/1999 | Stern et al. |
| 5,620,481 A | 4/1997 | Desai et al. | 5,908,444 A | 6/1999 | Azure |
| 5,626,575 A | 5/1997 | Crenner | 5,913,882 A | 6/1999 | King |
| 5,628,745 A | 5/1997 | Bek | 5,921,982 A | 7/1999 | Lesh et al. |
| 5,628,771 A | 5/1997 | Mizukawa et al. | 5,925,070 A | 7/1999 | King et al. |
| 5,640,113 A | 6/1997 | Hu | 5,931,836 A | 8/1999 | Hatta et al. |
| 5,643,330 A | 7/1997 | Holsheimer et al. | 5,935,124 A | 8/1999 | Klumb et al. |
| 5,647,869 A | 7/1997 | Goble et al. | 5,938,690 A | 8/1999 | Law et al. |
| 5,647,871 A | 7/1997 | Levine et al. | 5,944,553 A | 8/1999 | Yasui et al. |
| 5,651,780 A | 7/1997 | Jackson et al. | 5,948,007 A | 9/1999 | Starkebaum et al. |
| 5,658,322 A | 8/1997 | Fleming | 5,951,545 A | 9/1999 | Schilling |
| 5,660,567 A | 8/1997 | Nierlich et al. | 5,951,546 A | 9/1999 | Lorentzen |
| 5,664,953 A | 9/1997 | Reylek | 5,954,686 A | 9/1999 | Garito et al. |
| 5,674,217 A | 10/1997 | Wahlstrom et al. | 5,954,717 A | 9/1999 | Behl et al. |
| 5,678,568 A | 10/1997 | Uchikubo et al. | 5,954,719 A | 9/1999 | Chen et al. |
| 5,681,307 A | 10/1997 | McMahan | 5,957,961 A | 9/1999 | Maguire et al. |
| 5,685,840 A | 11/1997 | Schechter et al. | 5,957,969 A | 9/1999 | Warner et al. |
| 5,688,267 A | 11/1997 | Panescu et al. | 5,959,253 A | 9/1999 | Shinchi |
| 5,693,042 A | 12/1997 | Bioarski et al. | 5,961,344 A | 10/1999 | Rosales et al. |
| 5,693,078 A | 12/1997 | Desai et al. | 5,961,871 A | 10/1999 | Bible et al. |
| 5,694,304 A | 12/1997 | Telefus et al. | 5,964,746 A | 10/1999 | McCary |
| 5,695,494 A | 12/1997 | Becker | 5,971,980 A | 10/1999 | Sherman |
| 5,696,441 A | 12/1997 | Mak et al. | 5,971,981 A | 10/1999 | Hill et al. |
| 5,697,925 A | 12/1997 | Taylor | 5,976,128 A | 11/1999 | Schilling et al. |
| 5,697,927 A | 12/1997 | Imran et al. | 5,983,141 A | 11/1999 | Sluijter et al. |
| 5,702,386 A | 12/1997 | Stern et al. | 6,007,532 A | 12/1999 | Netherly |
| 5,702,429 A | 12/1997 | King | 6,010,499 A | 1/2000 | Cobb |
| 5,707,369 A | 1/1998 | Vaitekunas et al. | 6,013,074 A | 1/2000 | Taylor |
| 5,712,772 A | 1/1998 | Telefus et al. | 6,014,581 A | 1/2000 | Whayne et al. |
| 5,713,896 A | 2/1998 | Nardella | 6,017,338 A | 1/2000 | Brucker et al. |
| 5,718,246 A | 2/1998 | Vona | 6,017,354 A | 1/2000 | Culp et al. |
| 5,720,742 A | 2/1998 | Zacharias | 6,022,346 A | 2/2000 | Panescu et al. |
| 5,720,744 A | 2/1998 | Eggleston et al. | 6,022,347 A | 2/2000 | Lindenmeier et al. |
| 5,722,975 A | 3/1998 | Edwards et al. | 6,033,399 A | 3/2000 | Gines |
| 5,729,448 A | 3/1998 | Haynie et al. | 6,039,731 A | 3/2000 | Taylor et al. |
| 5,733,281 A | 3/1998 | Nardella | 6,039,732 A | 3/2000 | Ichikawa et al. |
| 5,735,846 A | 4/1998 | Panescu et al. | 6,041,260 A | 3/2000 | Stern et al. |
| 5,738,683 A | 4/1998 | Osypka | 6,044,283 A | 3/2000 | Fein et al. |
| 5,743,900 A | 4/1998 | Hara | 6,053,910 A | 4/2000 | Fleenor |
| 5,743,903 A | 4/1998 | Stern et al. | 6,053,912 A | 4/2000 | Panescu et al. |
| 5,749,869 A | 5/1998 | Lindenmeier et al. | 6,055,458 A | 4/2000 | Cochran et al. |
| 5,749,871 A | 5/1998 | Hood et al. | 6,056,745 A | 5/2000 | Panescu et al. |
| 5,755,715 A | 5/1998 | Stern | 6,056,746 A | 5/2000 | Goble et al. |
| 5,762,609 A | 6/1998 | Benaron et al. | 6,059,780 A | 5/2000 | Gough et al. |
| 5,766,153 A | 6/1998 | Eggers et al. | 6,059,781 A | 5/2000 | Yamanashi et al. |
| 5,766,165 A | 6/1998 | Gentelia et al. | 6,063,075 A | 5/2000 | Mihori |
| 5,769,847 A | 6/1998 | Panescu et al. | 6,063,078 A | 5/2000 | Wittkampf |
| 5,772,659 A | 6/1998 | Becker et al. | 6,066,137 A | 5/2000 | Greep |
| 5,777,519 A | 7/1998 | Simopoulos | 6,068,627 A | 5/2000 | Orszulak et al. |
| 5,788,688 A | 8/1998 | Bauer et al. | 6,074,089 A | 6/2000 | Hollander et al. |
| 5,792,138 A | 8/1998 | Shipp | 6,074,386 A | 6/2000 | Goble et al. |
| 5,797,902 A | 8/1998 | Netherly | 6,074,388 A | 6/2000 | Tockweiler et al. |
| 5,797,941 A | 8/1998 | Schulze et al. | 6,080,149 A | 6/2000 | Huang et al. |
| 5,807,253 A | 9/1998 | Dumoulin et al. | 6,088,614 A | 7/2000 | Swanson |
| 5,810,804 A | 9/1998 | Gough et al. | 6,089,864 A | 7/2000 | Buckner et al. |
| 5,814,092 A | 9/1998 | King | 6,090,123 A | 7/2000 | Culp et al. |
| 5,817,091 A | 10/1998 | Nardella et al. | 6,093,186 A | 7/2000 | Goble |
| 5,817,093 A | 10/1998 | Williamson, IV et al. | 6,102,497 A | 8/2000 | Ehr et al. |
| 5,820,568 A | 10/1998 | Willis | 6,102,907 A | 8/2000 | Smethers et al. |
| 5,827,271 A | 10/1998 | Buysse et al. | 6,104,248 A | 8/2000 | Carver |
| 5,830,212 A | 11/1998 | Cartmell | 6,106,524 A | 8/2000 | Eggers et al. |
| 5,831,166 A | 11/1998 | Kozuka et al. | 6,113,591 A | 9/2000 | Whayne et al. |
| 5,836,909 A | 11/1998 | Cosmescu | 6,113,592 A | 9/2000 | Taylor |
| 5,836,943 A | 11/1998 | Miller, III | 6,113,593 A | 9/2000 | Tu et al. |
| 5,836,990 A | 11/1998 | Li | 6,113,596 A | 9/2000 | Hooven |
| 5,843,019 A | 12/1998 | Eggers et al. | 6,123,701 A | 9/2000 | Nezhat |

| | | |
|---|---|---|
| 6,123,702 A | 9/2000 | Swanson et al. |
| 6,132,429 A | 10/2000 | Baker |
| 6,139,349 A | 10/2000 | Wright |
| 6,142,992 A | 11/2000 | Cheng et al. |
| 6,155,975 A | 12/2000 | Urich et al. |
| 6,162,184 A | 12/2000 | Swanson et al. |
| 6,162,217 A | 12/2000 | Kannenberg et al. |
| 6,165,169 A | 12/2000 | Panescu et al. |
| 6,165,173 A | 12/2000 | Kamdar et al. |
| 6,171,304 B1 | 1/2001 | Netherly et al. |
| 6,183,468 B1 | 2/2001 | Swanson et al. |
| 6,186,147 B1 | 2/2001 | Cobb |
| 6,188,211 B1 | 2/2001 | Rincon-Mora et al. |
| 6,193,713 B1 | 2/2001 | Geistert et al. |
| 6,197,023 B1 | 3/2001 | Muntermann |
| 6,203,541 B1 | 3/2001 | Keppel |
| 6,210,403 B1 | 4/2001 | Klicek |
| 6,216,704 B1 | 4/2001 | Ingle et al. |
| 6,222,356 B1 | 4/2001 | Taghizadeh-Kaschani |
| 6,228,078 B1 | 5/2001 | Eggers et al. |
| 6,228,080 B1 | 5/2001 | Gines |
| 6,228,081 B1 | 5/2001 | Goble |
| 6,231,569 B1 | 5/2001 | Bek |
| 6,232,556 B1 | 5/2001 | Daugherty et al. |
| 6,235,020 B1 | 5/2001 | Cheng et al. |
| 6,235,022 B1 | 5/2001 | Hallock et al. |
| 6,237,604 B1 | 5/2001 | Burnside et al. |
| 6,238,387 B1 | 5/2001 | Miller, III |
| 6,238,388 B1 | 5/2001 | Ellman |
| 6,241,723 B1 | 6/2001 | Heim et al. |
| 6,241,725 B1 | 6/2001 | Cosman |
| 6,243,654 B1 | 6/2001 | Johnson et al. |
| 6,245,061 B1 | 6/2001 | Panescu et al. |
| 6,245,063 B1 | 6/2001 | Uphoff |
| 6,245,065 B1 | 6/2001 | Panescu |
| 6,246,912 B1 | 6/2001 | Sluijter et al. |
| 6,251,106 B1 | 6/2001 | Becker et al. |
| 6,254,422 B1 | 7/2001 | Feye-Hohmann |
| 6,258,085 B1 | 7/2001 | Eggleston |
| 6,261,285 B1 | 7/2001 | Novak |
| 6,261,286 B1 | 7/2001 | Goble et al. |
| 6,267,760 B1 | 7/2001 | Swanson |
| 6,270,497 B1 | 8/2001 | Sekino et al. |
| 6,273,886 B1 | 8/2001 | Edwards |
| 6,275,786 B1 | 8/2001 | Daners |
| 6,287,304 B1 | 9/2001 | Eggers et al. |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,304,138 B1 | 10/2001 | Johnson |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,329,778 B1 | 12/2001 | Culp et al. |
| 6,337,998 B1 | 1/2002 | Behl et al. |
| 6,338,657 B1 | 1/2002 | Harper et al. |
| 6,341,981 B1 | 1/2002 | Gorman |
| 6,350,262 B1 | 2/2002 | Ashley |
| 6,358,245 B1 | 3/2002 | Edwards |
| 6,364,877 B1 | 4/2002 | Goble et al. |
| 6,370,408 B1 | 4/2002 | Merchant et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,424,186 B1 | 7/2002 | Quimby et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,469,481 B1 | 10/2002 | Tateishi |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,258 B2 | 4/2003 | Fleenor et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Bloom et al. |
| 6,623,423 B2 | 9/2003 | Ozaki et al. |
| 6,626,901 B1 | 9/2003 | Treat et al. |
| 6,629,973 B1 | 10/2003 | Wardell et al. |
| 6,629,974 B2 | 10/2003 | Penny et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Taylor et al. |
| 6,712,813 B2 | 3/2004 | Ellman |
| 6,723,091 B2 | 4/2004 | Goble et al. |
| 6,730,078 B2 | 5/2004 | Simpson et al. |
| 6,730,079 B2 | 5/2004 | Lovewell |

| | | | | | | |
|---|---|---|---|---|---|---|
| 6,730,080 | B2 | 5/2004 | Harano | RE39,358 | E | 10/2006 | Goble |
| 6,733,495 | B1 | 5/2004 | Bek | 7,115,121 | B2 | 10/2006 | Novak |
| 6,733,498 | B2 | 5/2004 | Paton | 7,115,124 | B1 | 10/2006 | Xiao |
| 6,740,079 | B1 | 5/2004 | Eggers | 7,118,564 | B2 | 10/2006 | Ritchie et al. |
| 6,740,085 | B2 | 5/2004 | Hareyama | 7,122,031 | B2 | 10/2006 | Edwards et al. |
| 6,743,225 | B2 | 6/2004 | Sanchez et al. | 7,131,445 | B2 | 11/2006 | Amoah |
| 6,746,284 | B1 | 6/2004 | Spink, Jr. | 7,131,860 | B2 | 11/2006 | Sartor et al. |
| 6,749,624 | B2 | 6/2004 | Knowlton | 7,137,980 | B2 | 11/2006 | Buysse et al. |
| 6,755,825 | B2 | 6/2004 | Shoenman et al. | 7,146,210 | B2 | 12/2006 | Palti |
| 6,758,846 | B2 | 7/2004 | Goble et al. | 7,147,638 | B2 | 12/2006 | Chapman et al. |
| 6,761,716 | B2 | 7/2004 | Kadhiresan et al. | 7,151,964 | B2 | 12/2006 | Desai et al. |
| 6,775,575 | B2 | 8/2004 | Bommannan et al. | 7,153,300 | B2 | 12/2006 | Goble |
| 6,778,044 | B2 | 8/2004 | Fehrenbach et al. | 7,156,842 | B2 | 1/2007 | Sartor et al. |
| 6,783,523 | B2 | 8/2004 | Qin | 7,156,844 | B2 | 1/2007 | Reschke et al. |
| 6,784,405 | B2 | 8/2004 | Flugstad et al. | 7,156,846 | B2 | 1/2007 | Dycus et al. |
| 6,786,905 | B2 | 9/2004 | Swanson et al. | 7,160,293 | B2 | 1/2007 | Sturm et al. |
| 6,790,206 | B2 | 9/2004 | Panescu | 7,163,536 | B2 | 1/2007 | Godara |
| 6,792,390 | B1 | 9/2004 | Burnside et al. | 7,166,986 | B2 | 1/2007 | Kendall |
| 6,796,980 | B2 | 9/2004 | Hall | 7,169,144 | B2 | 1/2007 | Hoey et al. |
| 6,796,981 | B2 | 9/2004 | Wham | 7,172,591 | B2 | 2/2007 | Harano et al. |
| 6,809,508 | B2 | 10/2004 | Donofrio | 7,175,618 | B2 | 2/2007 | Dabney et al. |
| 6,818,000 | B2 | 11/2004 | Muller et al. | 7,175,621 | B2 | 2/2007 | Heim et al. |
| 6,819,027 | B2 | 11/2004 | Saraf | 7,190,933 | B2 | 3/2007 | DeRuijter et al. |
| 6,824,539 | B2 | 11/2004 | Novak | 7,192,427 | B2 | 3/2007 | Chapelon et al. |
| 6,830,569 | B2 | 12/2004 | Thompson | 7,195,627 | B2 | 3/2007 | Amoah et al. |
| 6,837,888 | B2 | 1/2005 | Ciarrocca et al. | 7,200,010 | B2 | 4/2007 | Broman et al. |
| 6,843,682 | B2 | 1/2005 | Matsuda et al. | 7,203,556 | B2 | 4/2007 | Daners |
| 6,843,789 | B2 | 1/2005 | Goble | 7,204,835 | B2 | 4/2007 | Latterell et al. |
| 6,849,073 | B2 | 2/2005 | Hoey | 7,211,081 | B2 | 5/2007 | Goble |
| 6,855,141 | B2 | 2/2005 | Lovewell | 7,214,224 | B2 | 5/2007 | Goble |
| 6,855,142 | B2 | 2/2005 | Harano | 7,217,269 | B2 | 5/2007 | El-Galley et al. |
| 6,860,881 | B2 | 3/2005 | Sturm | 7,220,260 | B2 | 5/2007 | Fleming et al. |
| 6,864,686 | B2 | 3/2005 | Novak | 7,223,264 | B2 | 5/2007 | Daniel et al. |
| 6,875,210 | B2 | 4/2005 | Refior | 7,226,447 | B2 | 6/2007 | Uchida et al. |
| 6,890,331 | B2 | 5/2005 | Kristensen | 7,229,469 | B1 | 6/2007 | Witzel et al. |
| 6,893,435 | B2 | 5/2005 | Goble | 7,232,437 | B2 | 6/2007 | Berman et al. |
| 6,899,538 | B2 | 5/2005 | Matoba | 7,233,278 | B2 | 6/2007 | Eriksson |
| 6,923,804 | B2 | 8/2005 | Eggers et al. | 7,238,181 | B2 | 7/2007 | Daners et al. |
| 6,929,641 | B2 | 8/2005 | Goble et al. | 7,238,183 | B2 | 7/2007 | Kreindel |
| 6,936,047 | B2 | 8/2005 | Nasab et al. | 7,244,255 | B2 | 7/2007 | Daners et al. |
| 6,939,344 | B2 | 9/2005 | Kreindel | 7,247,155 | B2 | 7/2007 | Hoey et al. |
| 6,939,346 | B2 | 9/2005 | Kannenberg et al. | 7,250,048 | B2 | 7/2007 | Francischelli et al. |
| 6,939,347 | B2 | 9/2005 | Thompson | 7,250,746 | B2 | 7/2007 | Oswald et al. |
| 6,942,660 | B2 | 9/2005 | Pantera et al. | 7,255,694 | B2 | 8/2007 | Keppel |
| 6,948,503 | B2 | 9/2005 | Refior et al. | 7,258,688 | B1 | 8/2007 | Shah et al. |
| 6,953,461 | B2 | 10/2005 | McClurken et al. | 7,282,048 | B2 | 10/2007 | Goble et al. |
| 6,958,064 | B2 | 10/2005 | Rioux et al. | 7,282,049 | B2 | 10/2007 | Orszulak et al. |
| 6,962,587 | B2 | 11/2005 | Johnson et al. | 7,285,117 | B2 | 10/2007 | Krueger et al. |
| 6,966,907 | B2 | 11/2005 | Goble | 7,294,127 | B2 | 11/2007 | Leung et al. |
| 6,970,752 | B1 | 11/2005 | Lim et al. | 7,300,435 | B2 | 11/2007 | Wham et al. |
| 6,974,453 | B2 | 12/2005 | Woloszko et al. | 7,300,437 | B2 | 11/2007 | Pozzato |
| 6,974,463 | B2 | 12/2005 | Magers et al. | 7,303,557 | B2 | 12/2007 | Wham et al. |
| 6,977,495 | B2 | 12/2005 | Donofrio | 7,305,311 | B2 | 12/2007 | Van Zyl |
| 6,984,231 | B2 | 1/2006 | Goble et al. | 7,311,703 | B2 | 12/2007 | Turovskiy et al. |
| 6,989,010 | B2 | 1/2006 | Francischelli et al. | 7,316,682 | B2 | 1/2008 | Konesky |
| 6,994,704 | B2 | 2/2006 | Qin et al. | 7,317,954 | B2 | 1/2008 | McGreevy |
| 6,994,707 | B2 | 2/2006 | Ellman et al. | 7,317,955 | B2 | 1/2008 | McGreevy |
| 7,001,379 | B2 | 2/2006 | Behl et al. | 7,324,357 | B2 | 1/2008 | Miura et al. |
| 7,001,381 | B2 | 2/2006 | Harano et al. | 7,333,859 | B2 | 2/2008 | Rinaldi et al. |
| 7,004,174 | B2 | 2/2006 | Eggers et al. | 7,341,586 | B2 | 3/2008 | Daniel et al. |
| 7,008,369 | B2 | 3/2006 | Cuppen | 7,344,532 | B2 | 3/2008 | Goble et al. |
| 7,008,417 | B2 | 3/2006 | Eick | 7,353,068 | B2 | 4/2008 | Tanaka et al. |
| 7,008,421 | B2 | 3/2006 | Daniel et al. | 7,354,436 | B2 | 4/2008 | Rioux et al. |
| 7,025,764 | B2 | 4/2006 | Paton et al. | 7,357,800 | B2 | 4/2008 | Swanson |
| 7,033,351 | B2 | 4/2006 | Howell | 7,364,577 | B2 | 4/2008 | Wham et al. |
| 7,041,096 | B2 | 5/2006 | Malis et al. | 7,364,578 | B2 | 4/2008 | Francischelli et al. |
| 7,044,948 | B2 | 5/2006 | Keppel | 7,364,972 | B2 | 4/2008 | Ono et al. |
| 7,044,949 | B2 | 5/2006 | Orszulak et al. | 7,367,972 | B2 | 5/2008 | Francischelli et al. |
| 7,048,687 | B1 | 5/2006 | Reuss et al. | RE40,388 | E | 6/2008 | Gines |
| 7,058,372 | B1 | 6/2006 | Pardoen et al. | 7,396,336 | B2 | 7/2008 | Orszulak et al. |
| 7,060,063 | B2 | 6/2006 | Marion et al. | 7,402,754 | B2 | 7/2008 | Kirwan, Jr. et al. |
| 7,062,331 | B2 | 6/2006 | Zarinetchi et al. | D574,323 | S | 8/2008 | Waaler |
| 7,063,692 | B2 | 6/2006 | Sakurai et al. | 7,407,502 | B2 | 8/2008 | Strul et al. |
| 7,066,933 | B2 | 6/2006 | Hagg | 7,416,437 | B2 | 8/2008 | Sartor et al. |
| 7,074,217 | B2 | 7/2006 | Strul et al. | 7,416,549 | B2 | 8/2008 | Young et al. |
| 7,083,618 | B2 | 8/2006 | Couture et al. | 7,422,582 | B2 | 9/2008 | Malackowski et al. |
| 7,087,054 | B2 | 8/2006 | Truckai et al. | 7,422,586 | B2 | 9/2008 | Morris et al. |
| 7,094,231 | B1 | 8/2006 | Ellman et al. | 7,425,835 | B2 | 9/2008 | Eisele |
| 7,104,834 | B2 | 9/2006 | Robinson et al. | 7,465,302 | B2 | 12/2008 | Odell et al. |

| Patent/Publication No. | Date | Inventor(s) |
|---|---|---|
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,511,472 B1 | 3/2009 | Xia et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,568,619 B2 | 8/2009 | Todd et al. |
| 7,582,084 B2 | 9/2009 | Swanson et al. |
| 7,621,041 B2 | 11/2009 | Banerji et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 7,655,003 B2 | 2/2010 | Lorang et al. |
| 7,675,429 B2 | 3/2010 | Cernasov |
| 7,678,105 B2 | 3/2010 | McGreevy et al. |
| 7,722,601 B2 | 5/2010 | Wham et al. |
| 7,731,717 B2 | 6/2010 | Odom et al. |
| 7,736,358 B2 | 6/2010 | Shores et al. |
| 7,744,593 B2 | 6/2010 | Mihori |
| 7,749,217 B2 | 7/2010 | Podhajsky |
| 7,766,693 B2 | 8/2010 | Sartor et al. |
| 7,766,905 B2 | 8/2010 | Paterson et al. |
| 7,780,662 B2 | 8/2010 | Bahney |
| 7,780,764 B2 | 8/2010 | Baksh |
| 7,794,457 B2 | 9/2010 | McPherson et al. |
| 7,799,020 B2 | 9/2010 | Shores et al. |
| 7,799,026 B2 | 9/2010 | Schechter et al. |
| 7,824,400 B2 | 11/2010 | Keppel |
| 7,834,484 B2 | 11/2010 | Sartor |
| 7,863,841 B2 | 1/2011 | Menegoli et al. |
| 7,864,129 B2 | 1/2011 | Konishi |
| 7,901,400 B2 | 3/2011 | Wham et al. |
| 7,927,328 B2 | 4/2011 | Orszulak et al. |
| 7,947,039 B2 | 5/2011 | Sartor |
| 7,956,620 B2 | 6/2011 | Gilbert |
| 7,959,626 B2 | 6/2011 | Hong et al. |
| 7,972,328 B2 | 7/2011 | Wham et al. |
| 7,972,332 B2 | 7/2011 | Arts et al. |
| 7,976,544 B2 | 7/2011 | McClurken et al. |
| 8,004,121 B2 | 8/2011 | Sartor |
| 8,012,150 B2 | 9/2011 | Wham et al. |
| 8,025,660 B2 | 9/2011 | Plaven et al. |
| 8,034,049 B2 | 10/2011 | Odom et al. |
| 2002/0029036 A1 | 3/2002 | Goble et al. |
| 2003/0153908 A1 | 8/2003 | Goble et al. |
| 2003/0181898 A1 | 9/2003 | Bowers |
| 2003/0229344 A1 | 12/2003 | Dycus et al. |
| 2004/0015159 A1 | 1/2004 | Slater et al. |
| 2004/0030330 A1 | 2/2004 | Brassell et al. |
| 2004/0068304 A1 | 4/2004 | Paton |
| 2004/0097912 A1 | 5/2004 | Gonnering |
| 2004/0133189 A1 | 7/2004 | Sakurai |
| 2004/0172016 A1 | 9/2004 | Bek et al. |
| 2005/0004634 A1 | 1/2005 | Ricart et al. |
| 2005/0021020 A1 | 1/2005 | Blaha et al. |
| 2005/0109111 A1 | 5/2005 | Manlove et al. |
| 2005/0131390 A1 | 6/2005 | Heinrich et al. |
| 2006/0015095 A1 | 1/2006 | Desinger et al. |
| 2006/0079774 A1 | 4/2006 | Anderson |
| 2006/0111711 A1 | 5/2006 | Goble |
| 2006/0161148 A1 | 7/2006 | Behnke |
| 2006/0224152 A1 | 10/2006 | Behnke et al. |
| 2006/0291178 A1 | 12/2006 | Shih |
| 2007/0038209 A1 | 2/2007 | Buysse et al. |
| 2007/0088413 A1 | 4/2007 | Weber et al. |
| 2007/0093801 A1 | 4/2007 | Behnke |
| 2007/0129716 A1 | 6/2007 | Daw et al. |
| 2007/0173802 A1 | 7/2007 | Keppel |
| 2007/0173803 A1 | 7/2007 | Wham et al. |
| 2007/0173805 A1 | 7/2007 | Weinberg et al. |
| 2007/0173811 A1 | 7/2007 | Couture et al. |
| 2007/0173813 A1 | 7/2007 | Odom |
| 2007/0203481 A1 | 8/2007 | Gregg et al. |
| 2007/0265612 A1 | 11/2007 | Behnke et al. |
| 2007/0282320 A1 | 12/2007 | Buysse et al. |
| 2007/0293858 A1 | 12/2007 | Fischer |
| 2008/0004619 A1 | 1/2008 | Malis et al. |
| 2008/0015563 A1 | 1/2008 | Hoey et al. |
| 2008/0015564 A1 | 1/2008 | Wham et al. |
| 2008/0015570 A1 | 1/2008 | Ormsby et al. |
| 2008/0071257 A1 | 3/2008 | Kotmel et al. |
| 2008/0071260 A1 | 3/2008 | Shores |
| 2008/0119843 A1 | 5/2008 | Morris |
| 2008/0125767 A1 | 5/2008 | Blaha |
| 2008/0132893 A1 | 6/2008 | D'Amelio et al. |
| 2008/0177199 A1 | 7/2008 | Podhajsky |
| 2008/0188849 A1 | 8/2008 | Goldberg et al. |
| 2008/0203997 A1 | 8/2008 | Foran et al. |
| 2008/0262489 A1 | 10/2008 | Steinke |
| 2008/0281311 A1 | 11/2008 | Dunning et al. |
| 2008/0281315 A1 | 11/2008 | Gines |
| 2008/0281316 A1 | 11/2008 | Carlton et al. |
| 2008/0287791 A1 | 11/2008 | Orszulak et al. |
| 2008/0287838 A1 | 11/2008 | Orszulak et al. |
| 2008/0287943 A1 | 11/2008 | Weber et al. |
| 2009/0018536 A1 | 1/2009 | Behnke |
| 2009/0036883 A1 | 2/2009 | Behnke |
| 2009/0069801 A1 | 3/2009 | Jensen et al. |
| 2009/0082765 A1 | 3/2009 | Collins et al. |
| 2009/0146635 A1 | 6/2009 | Qiu et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0157075 A1 | 6/2009 | Wham et al. |
| 2009/0234350 A1 | 9/2009 | Behnke et al. |
| 2009/0237169 A1 | 9/2009 | Orszulak |
| 2009/0240244 A1 | 9/2009 | Malis et al. |
| 2009/0248003 A1 | 10/2009 | Orszulak |
| 2009/0248006 A1 | 10/2009 | Paulus et al. |
| 2009/0254077 A1 | 10/2009 | Craig |
| 2009/0259224 A1 | 10/2009 | Wham et al. |
| 2009/0292283 A1 | 11/2009 | Odom |
| 2009/0299360 A1 | 12/2009 | Ormsby |
| 2009/0306648 A1 | 12/2009 | Podhajsky et al. |
| 2010/0030210 A1 | 2/2010 | Paulus |
| 2010/0042093 A9 | 2/2010 | Wham et al. |
| 2010/0057076 A1 | 3/2010 | Behnke et al. |
| 2010/0063494 A1 | 3/2010 | Orszulak |
| 2010/0063497 A1 | 3/2010 | Orszulak |
| 2010/0076424 A1 | 3/2010 | Carr |
| 2010/0079215 A1 | 4/2010 | Brannan et al. |
| 2010/0082023 A1 | 4/2010 | Haley et al. |
| 2010/0082023 A1 | 4/2010 | Brannan et al. |
| 2010/0082024 A1 | 4/2010 | Brannan et al. |
| 2010/0082025 A1 | 4/2010 | Brannan et al. |
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094275 A1 | 4/2010 | Wham |
| 2010/0094288 A1 | 4/2010 | Kerr |
| 2010/0179529 A1 | 7/2010 | Podhajsky et al. |
| 2010/0179533 A1 | 7/2010 | Podhajsky |
| 2010/0179534 A1 | 7/2010 | Podhajsky et al. |
| 2010/0179535 A1 | 7/2010 | Podhajsky et al. |
| 2010/0179536 A1 | 7/2010 | Podhajsky et al. |
| 2010/0179538 A1 | 7/2010 | Podhajsky |
| 2010/0179541 A1 | 7/2010 | Joseph et al. |
| 2010/0179542 A1 | 7/2010 | Joseph et al. |
| 2010/0191233 A1 | 7/2010 | Wham et al. |
| 2010/0211063 A1 | 8/2010 | Wham et al. |
| 2010/0217258 A1 | 8/2010 | Floume et al. |
| 2010/0217264 A1 | 8/2010 | Odom et al. |
| 2010/0318079 A1 | 12/2010 | McPherson et al. |
| 2010/0318080 A1 | 12/2010 | Keppel |
| 2011/0028963 A1 | 2/2011 | Gilbert |
| 2011/0054460 A1 | 3/2011 | Gilbert |
| 2011/0060329 A1 | 3/2011 | Gilbert |
| 2011/0071516 A1 | 3/2011 | Gregg |
| 2011/0071521 A1 | 3/2011 | Gilbert |
| 2011/0077631 A1 | 3/2011 | Keller |
| 2011/0112530 A1 | 5/2011 | Keller |
| 2011/0115562 A1 | 5/2011 | Gilbert |
| 2011/0144635 A1 | 6/2011 | Harper et al. |

| | | | | | |
|---|---|---|---|---|---|
| 2011/0178516 A1 | 7/2011 | Orszulak et al. | EP | 1263181 | 9/2008 |
| 2011/0202056 A1 | 8/2011 | Sartor | EP | 2253286 | 11/2010 |
| 2011/0204903 A1 | 8/2011 | Gilbert | EP | 1594392 | 6/2011 |
| 2011/0208179 A1 | 8/2011 | Prakash et al. | FR | 1275415 | 10/1961 |
| 2011/0213354 A1 | 9/2011 | Smith | FR | 1347865 | 11/1963 |
| 2011/0213355 A1 | 9/2011 | Behnke, II | FR | 2313708 | 12/1976 |
| | | | FR | 2364461 | 7/1978 |
| FOREIGN PATENT DOCUMENTS | | | FR | 2502935 | 10/1982 |
| | | | FR | 2517953 | 6/1983 |
| DE | 1139927 | 11/1962 | FR | 2573301 | 5/1986 |
| DE | 1149832 | 6/1963 | GB | 607850 | 9/1948 |
| DE | 1439302 | 1/1969 | GB | 702510 | 1/1954 |
| DE | 2439587 | 2/1975 | GB | 855459 | 11/1960 |
| DE | 2455174 | 5/1975 | GB | 902775 | 8/1962 |
| DE | 2407559 | 8/1975 | GB | 2154881 | 9/1985 |
| DE | 2602517 | 7/1976 | GB | 2164473 | 3/1986 |
| DE | 2504280 | 8/1976 | GB | 2214430 | 9/1989 |
| DE | 2540968 | 3/1977 | GB | 2331247 | 5/1999 |
| DE | 2820908 | 11/1978 | GB | 2358934 | 8/2001 |
| DE | 2803275 | 8/1979 | GB | 2434872 | 8/2007 |
| DE | 2823291 | 11/1979 | SU | 166452 | 1/1965 |
| DE | 2946728 | 5/1981 | SU | 727201 | 4/1980 |
| DE | 3143421 | 5/1982 | WO | WO92/06642 | 4/1992 |
| DE | 3045996 | 7/1982 | WO | WO92/07622 | 5/1992 |
| DE | 3120102 | 12/1982 | WO | WO93/24066 | 12/1993 |
| DE | 3510586 | 10/1986 | WO | WO94/10922 | 5/1994 |
| DE | 3604823 | 8/1987 | WO | WO94/24949 | 11/1994 |
| DE | 390937 | 4/1989 | WO | WO94/28809 | 12/1994 |
| DE | 3904558 | 8/1990 | WO | WO95/09577 | 4/1995 |
| DE | 3942998 | 7/1991 | WO | WO95/18575 | 7/1995 |
| DE | 4206433 | 9/1993 | WO | WO95/19148 | 7/1995 |
| DE | 4339049 | 5/1995 | WO | WO95/25471 | 9/1995 |
| DE | 19506363 | 8/1996 | WO | WO95/25472 | 9/1995 |
| DE | 19717411 | 11/1998 | WO | WO96/02180 | 2/1996 |
| DE | 19848540 | 5/2000 | WO | WO96/04860 | 2/1996 |
| EP | 246350 | 11/1987 | WO | WO96/08794 | 3/1996 |
| EP | 267403 | 5/1988 | WO | WO96/18349 | 6/1996 |
| EP | 296777 | 12/1988 | WO | WO96/29946 | 10/1996 |
| EP | 310431 | 4/1989 | WO | WO96/39085 | 12/1996 |
| EP | 325456 | 7/1989 | WO | WO96/39086 | 12/1996 |
| EP | 336742 | 10/1989 | WO | WO96/39088 | 12/1996 |
| EP | 390937 | 10/1990 | WO | WO96/39914 | 12/1996 |
| EP | 556705 | 8/1993 | WO | WO97/06739 | 2/1997 |
| EP | 569130 | 11/1993 | WO | WO97/06740 | 2/1997 |
| EP | 608609 | 8/1994 | WO | WO97/06855 | 2/1997 |
| EP | 640317 | 3/1995 | WO | WO97/10763 | 3/1997 |
| EP | 694291 | 1/1996 | WO | WO97/11648 | 4/1997 |
| EP | 617925 | 7/1996 | WO | WO97/17029 | 5/1997 |
| EP | 836868 | 4/1998 | WO | WO97/43971 | 11/1997 |
| EP | 878169 | 11/1998 | WO | WO98/07378 | 2/1998 |
| EP | 882955 | 12/1998 | WO | WO98/18395 | 5/1998 |
| EP | 1051948 | 11/2000 | WO | WO98/27880 | 7/1998 |
| EP | 1053720 | 11/2000 | WO | WO99/12607 | 3/1999 |
| EP | 1151725 | 11/2001 | WO | WO99/56647 | 11/1999 |
| EP | 1278007 | 1/2003 | WO | WO00/48672 | 8/2000 |
| EP | 1293171 | 3/2003 | WO | WO00/54683 | 9/2000 |
| EP | 1472984 | 11/2004 | WO | WO01/01847 | 1/2001 |
| EP | 1495712 | 1/2005 | WO | WO02/00129 | 1/2002 |
| EP | 1500378 | 1/2005 | WO | WO02/11634 | 2/2002 |
| EP | 1146827 | 3/2005 | WO | WO02/32333 | 4/2002 |
| EP | 1535581 | 6/2005 | WO | WO02/45589 | 6/2002 |
| EP | 870473 | 9/2005 | WO | WO02/47565 | 6/2002 |
| EP | 1609430 | 12/2005 | WO | WO02/053048 | 7/2002 |
| EP | 1366724 | 1/2006 | WO | WO02/088128 | 7/2002 |
| EP | 1707144 | 3/2006 | WO | WO03/047446 | 6/2003 |
| EP | 1645235 | 4/2006 | WO | WO03/090630 | 11/2003 |
| EP | 880220 | 6/2006 | WO | WO03/090635 | 11/2003 |
| EP | 1681026 | 7/2006 | WO | WO03/092520 | 11/2003 |
| EP | 1707143 | 10/2006 | WO | WO2004/028385 | 4/2004 |
| EP | 1744354 | 1/2007 | WO | WO2004/098385 | 4/2004 |
| EP | 1776929 | 4/2007 | WO | WO2004/043240 | 5/2004 |
| EP | 1810628 | 7/2007 | WO | WO2004/047659 | 6/2004 |
| EP | 1810630 | 7/2007 | WO | WO2004/052182 | 6/2004 |
| EP | 1810631 | 7/2007 | WO | WO2004/073488 | 9/2004 |
| EP | 1810632 | 7/2007 | WO | WO2004/103156 | 12/2004 |
| EP | 1810633 | 7/2007 | WO | WO2005/046496 | 5/2005 |
| EP | 1810634 | 7/2007 | WO | WO2005/048809 | 6/2005 |
| EP | 1854423 | 11/2007 | WO | WO2005/050151 | 6/2005 |
| EP | 1862137 | 12/2007 | WO | WO2005/060365 | 7/2005 |
| EP | 2025297 | 5/2008 | | | |

| | | |
|---|---|---|
| WO | WO2005/060849 | 7/2005 |
| WO | WO2005/115235 | 12/2005 |
| WO | WO2005/117735 | 12/2005 |
| WO | WO2006/050888 | 5/2006 |
| WO | WO2006/105121 | 10/2006 |
| WO | WO2007/055491 | 5/2007 |
| WO | WO2007/067522 | 6/2007 |
| WO | WO2007/105963 | 9/2007 |
| WO | WO2008/002517 | 1/2008 |
| WO | WO2008/003058 | 1/2008 |
| WO | WO2008/011575 | 1/2008 |
| WO | WO2008/043999 | 4/2008 |
| WO | WO2008/044000 | 4/2008 |
| WO | WO2008/044013 | 4/2008 |
| WO | WO2008/053532 | 5/2008 |
| WO | WO2008/070562 | 6/2008 |
| WO | WO2008/071914 | 6/2008 |
| WO | WO2008/110756 | 9/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Coutur.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Plaven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.
Wald et al., "Accidental Burns", Jama, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report Pp 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.

International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
US 6,878,148, 04/2005, Goble (withdrawn)

SYSTEM AND METHOD FOR CLOSED LOOP MONITORING OF MONOPOLAR ELECTROSURGICAL APPARATUS

CROSS-REFERENCE TO RELATED APPLICATION

The present application is a continuation of U.S. application Ser. No. 13/074,769 filed on Mar. 29, 2011, which is a continuation of U.S. application Ser. No. 11/657,174 filed on Jan. 24, 2007, which claims priority to U.S. Provisional Application Ser. No. 60/761,440 filed on Jan. 24, 2006, the entire contents of both of which are incorporated by reference herein.

BACKGROUND

1. Field

The present disclosure relates generally to electrosurgical system and method, more specifically, to a system and method for closed loop monitoring of monopolar electrosurgical apparatus to sense tissue and energy properties and control energy delivery based on the sensed properties.

2. Description of the Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active (current supplying) electrode such that an electrical circuit is formed between the two electrodes. Commonly, electrodes in bipolar electrosurgical systems are disposed within electrosurgical forceps, which lend itself particularly well to vessel sealing. In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Electrosurgical generators are capable of producing a variety of electrical waveforms. Certain waveforms are better suited for specific electrosurgical procedures. A continuous waveform having a duty cycle of 100% is best suited for cutting the tissue since the energy produces heat very rapidly thereby vaporizing the tissue. An intermittent waveform, where the duty cycle of about 10% is best suited for coagulating the tissue since the amount of heat generated is reduced.

Currently parameters affecting the coagulation waveform are adjusted manually by the surgeon. This adjustment process is cumbersome since the coagulation waveform may need to be adjusted continuously during its delivery. However, there are no systems available which can adjust the coagulation waveform automatically.

SUMMARY

The present disclosure provides for an electrosurgical system having closed loop monitoring. The system includes an electrosurgical generator having an RF output stage for generating electrosurgical waveforms suitable for coagulation and a microprocessor for controlling the RF output stage. The closed loop monitoring includes a sensor for sensing one or more tissue properties, such as voltage, current, temperature. The sensor transmits data pertaining to the tissue properties to the microprocessor which adjusts generator output. More specifically, the generator adjusts the electrosurgical waveforms in response to the data to correspond with predetermined waveform parameters.

An electrosurgical system is also disclosed, which is configured to provide automatic closed loop control of the RF energy in direct response to tissue changes until a desired clinical hemostasis effect is achieved. The system includes a generator having a high speed high voltage power source ("HVPS") for supplying direct current ("DC") output. The HVPS is configured to adjust DC output in a rapid and dynamic fashion. The generator includes an RF output stage which is configured to generate radio frequency ("RF") energy comprising one or more electrosurgical coagulation waveforms suitable for coagulating tissue. The system also includes an RF sensor for sensing properties of the RF energy and generating an RF signal indicative of the RF energy. The sampling rates for sensing are sufficient to allow the generator to sculpt the electrosurgical coagulation waveforms in real time as a function of the RF sensor signal in order to match the waveforms to the RF stage. The system further includes a closed loop control system which controls the electrosurgical coagulation waveform. Additionally, the system includes one or more gain controllers configured to amplify the RF sensor signal to maintain a predetermined signal to noise ratio and to provide RF voltage and current correction of the RF sensor signal which is then transmitted to the controller to allow for real time modification of RF energy.

According to one aspect of the present disclosure an electrosurgical system is disclosed which includes a generator configured to generate electrosurgical coagulation waveforms. The generator includes a closed loop control system which controls the electrosurgical coagulation waveforms. The closed loop control system includes a sensor configured to sense a tissue property or an energy property and transmit the tissue property or an energy property as one or more sensor signals having an amplitude. The control system also includes a gain controller configured to process the sensor signals to reduce the amplitude thereof and to obtain a signal to noise ratio of the sensor signals within a predetermine range. Microprocessor is coupled to the generator and is configured to adjust the electrosurgical coagulation waveforms as a function of the sensor signals.

According to another aspect of the present disclosure a closed loop control system for controlling electrosurgical coagulation waveforms is disclosed. The closed loop control system includes a sensor configured to sense a tissue property or an energy property and transmit the tissue property or energy property as one or more sensor signals having an amplitude. The control system also includes a gain controller configured to process the sensor signals to reduce the amplitude thereof and to obtain a signal to noise ratio of the sensor signals within a predetermine range. Microprocessor is coupled to the generator and is configured to adjust the electrosurgical coagulation waveforms as a function of the sensor signals.

A method for controlling electrosurgical coagulation waveforms is also contemplated by the present disclosure. The method includes the steps of sensing a tissue property or an energy property and transmitting the tissue property or an energy property as sensor signals having an amplitude and processing the sensor signals to reduce the amplitude thereof and to obtain a signal to noise ratio of the sensor signals within a predetermine range. The method also includes the step of adjusting the electrosurgical coagulation waveforms as a function of the sensor signals.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

The present disclosure provides for an electrosurgical system having precision closed loop monitoring of tissue and energy properties. The system includes a generator which is configured for high-speed power sourcing of radio frequency (RF) energy. The control loop includes a plurality of sensors for sensing tissue and energy properties and gain control for modifying generator output. The sensors monitor tissue properties in real time to allow an embedded controller to provide corrective adjustment to the delivered RF energy. The closed control loop automatically corrects the applied RF energy, based on tissue and energy properties according to prescribed algorithm determined by the clinical procedure. The generator receives the corrective adjustment from the controller and dynamically modifies the delivered energy in direct response to changes in tissue properties until a desired clinical effect is achieved.

Figure 1:
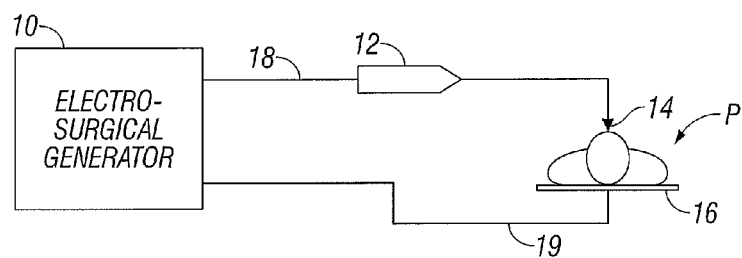
FIG. 1 is a schematic block diagram of an electrosurgical system.

FIG. 1 is a schematic illustration of an electrosurgical system 1 configured for a monopolar procedure. The system 1 includes an active electrode 14 and a return electrode 16 for treating tissue of a patient P. Electrosurgical RF energy is supplied to the active electrode 14 by a generator 10 via a cable 18 allowing the active electrode 14 to ablate, cut or coagulate the tissue. The return electrode 16 is placed at the patient P to return the energy from the patient P to the generator 10 via a cable 19.

The generator 10 includes input controls (e.g., buttons, activators, switches, etc.) for controlling the generator 10. The controls allow the surgeon to adjust power of the RF energy, waveform, and other parameters to achieve the desired waveform suitable for a particular task (e.g., cutting, coagulating, etc.). Disposed between the generator 10 and the active electrode 14 on the cable 18 is a hand piece 12, which includes a plurality of input controls which may be redundant with certain input controls of the generator 10. Placing the input controls at the hand piece 12 allows for easier and faster modification of RF energy parameters during the surgical procedure without returning to the generator 10. It is also envisioned that a footswitch may be connected to the generator 10 to control energy delivery during monopolar procedures. It is further envisioned that the hand piece 12 and the electrode 14 can be incorporated into a single instrument e.g., a surgical pencil, with the electrode 14 being disposed at a distal end of the hand piece 12.

Figure 2:
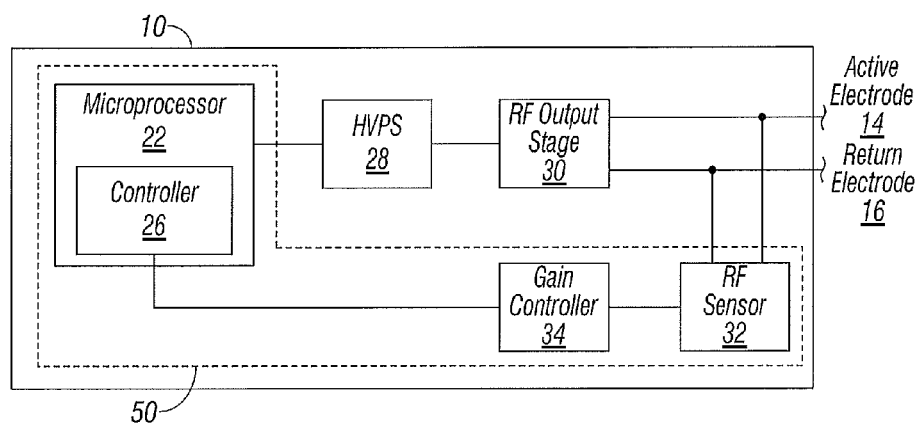
FIG. 2 is a schematic block diagram of a generator according to the present disclosure.

FIG. 2 shows a schematic block diagram of the generator 10 having a microprocessor 22, a high voltage DC power supply ("HVPS") 28, an RF output stage 30, at least one RF sensor 32 configured to measure one or more tissue and/or energy properties, and a gain controller 34. The microprocessor 22 includes a controller 26 and an output port which is electrically connected to the HVPS 28 configured to supply DC voltage, from about 0 V to about 200 V, to the RF output stage 30. The microprocessor 22 receives input signals from the generator 10, the hand piece 12, or the footswitch and the controller 26, in turn, adjusts output parameters of the generator 10, more specifically the HVPS 28, and/or performs other control functions thereon. It is also envisioned that the controller 26 is configured to receive control signals from the gain controller 34 for dynamic adjustment to the RF energy being delivered to the tissue.

The RF output stage 30 converts DC power into RF energy and delivers the RF energy, at about 470 KHz, to the active electrode 14 or other electrosurgical devices connected to the generator 10. In addition, the RF output stage 30 also receives RF energy from the return electrode 16. The RF sensor 32 is connected to the input and output (e.g., the connections to the active electrode 14 and the return electrode 16) of the RF output stage 30 to sense tissue and energy properties (e.g., impedance, voltage, current, temperature, phase, voltage peak, crest factor, current peak, real and reactive power, voltage rate change over time [dv/dt], phase rate change over time [dφ/dt], current rate change over time [dI/dt], temperature rate change over time [dT/dt], impedance rate change over time [dz/dt], high order harmonics of the fundamental 472 kHz waveform, etc.)

The generator 10 includes a closed loop control system 50 having the microprocessor 22, the controller 26, the RF sensor 32 and the gain controller 34 along with components thereof shown in FIGS. 3A-B and discussed in more detail below. The RF sensor 32 transmits signals representing tissue and/or energy properties through the gain control 34 to adjust the RF energy output accordingly. Sensed properties are transmitted to the microprocessor 22 and the controller 26 to perform calculations to determine the adjustments which have to be made to the RF energy output. The microprocessor 22 compares impedance, voltage, and other measurements to desired values and signals the RF output stage 30 to make any adjustments necessary to achieve the desired values.

In addition to impedance and voltage, the microprocessor 22 also measures voltage at a peak of the waveform (Vpk) and root-mean-square voltage (Vrms). Peak and rms calculations are also performed using current (I) value. To calculate rms values, the sample rates of the voltage and current signals must correspond to the buffer size of the sensor 32. More specifically, the microprocessor 22 includes a buffer which is sized so that it contains an integer number of full cycles of the waveform at a specified sample rate to avoid modulation errors within the rms values. This allows the sensor 32 to tailor the data acquisition to the varied waveforms associated with coagulation RF energy.

The microprocessor 22 calculates crest factor (Vpk/Vrms or Ipk/Irms) and V and I peak values in real time and controls output waveform timing and RF amplitude as a function thereof. It is envisioned that real time calculation of crest factor can be used to adjust the RF energy or adjust the waveform to keep a crest factor profile. More specifically, real time calculation of crest factor allows for coagulation modes to be controlled by adjusting the output RF energy to maintain a predetermined crest factor. Either crest factor or V and I peak values can be held constant and adjust the output waveform timing and RF amplitude accordingly.

The gain controller 34 processes sensed voltage and current signals received from the RF sensor 32. More specifically, the gain controller 34 reduces high amplitudes of coagulation voltage and current signals which allows for the signals to be transmitted into the microprocessor 22 for processing. The gain control 34 provides for both amplification and attenuation of the voltage and current signals to obtain good signal to noise ratios to minimize bit quantization error. Resolution and accuracy of the sensed RF delivered to precisely control the patient energy dosage.

Figure 3A:
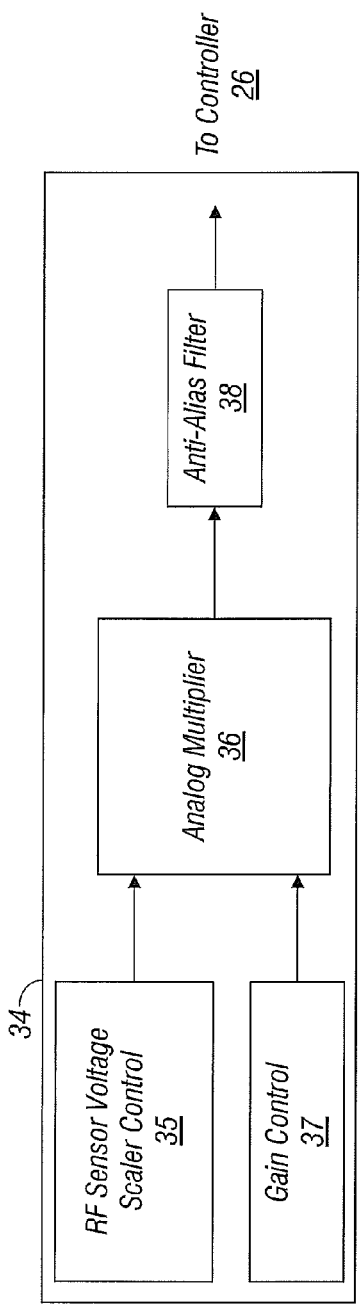
FIGS. 3A-B are a schematic block diagrams of closed loop coagulation control according to the present disclosure.
Figure 3B:
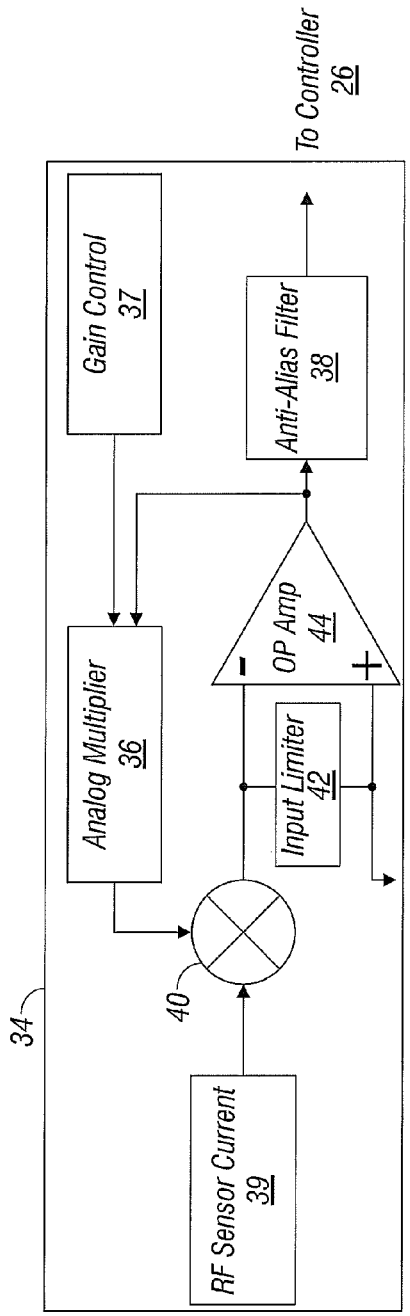

With reference to FIGS. 3A-B, the gain control process is illustrated in two embodiments. FIG. 3A, shows the gain controller 34 which includes RF sensor voltage scaler control 35 and a gain control 37 connected to an analog multiplier 36 which is then connected to an anti-alias filter 38. In this embodiment, the gain controller 34 adjusts the sensed voltage of the RF energy. The voltage scaler 35 which receives RF signals (e.g., signals representative of the RF energy being outputted by the generator 10) from the RF sensor 32 and dynamically and automatically scales the RF signal to adjust the high amplitude levels of the RF coagulation voltage and current signals. The gain control 37 provides real time gain modification of the RF energy by processing a variable DC level control signal received from the controller 26. The analog multiplier 36 performs a real time multiplication of signal inputs received from the outputs of the voltage scaler 35 and the gain control 37. The analog multiplier 36 normalizes the RF sensor signals independent of the high amplitude levels of the RF output 30 to maximize the precision of the delivered RF energy.

The anti-alias filter 38 blocks the RF frequency harmonics from contributing errors to the computed processing performed by the controller 26. The filter 38 processes the RF energy to reduce RF noise components and increase the accuracy of the delivered RF energy to the patient. It is also envisioned that the RF sensor 32 also includes an amplitude reduction circuit (not shown) to protect the front end of the multiplier 44.

FIG. 3B shows another embodiment of the gain controller 34 which includes an RF sensor current scaler control 39. In this embodiment, the gain controller 34 adjusts the sensed current of the RF energy. Gain control 37 is connected to the analog multiplier 36 and anti-alias filter components in similar manner as shown in FIG. 3A and discussed above. The output from the anti-alias filter 38 is fed to the output line (e.g., leading to the controller 26). In FIG. 3B, the output of the analog multiplier 36 is current mapped 1:1 to the RF sensor current input received from the RF sensor 32. Summer 40 processes the difference signals between the analog multiplier 36 and the RF sensor current input in conjunction with an operational amplifier ("OP amp") 44 to create an equivalent normalized RF output signal independent of the high amplitude levels of the RF output stage 30. Input limiter 42 provides surge protection to the OP amp 44 input, to increase the reliability of the gain controller 34.

The generator 10 is capable of making small adjustments to the RF waveform of high resolution (e.g., 10 ns). This allows control of crest factor and peak outputs as well as tuning of the output waveforms so that the output frequency can be adjusted to match the resonant frequency of the RF output stage 30. The generator 10 is configured to sculpt output curves to a degree using a linear interpolation method which allows any curve described within a predetermined number of points (e.g., 15), where the curves represent either current, power, voltage etc.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical generator configured to generate at least one electrosurgical waveform, the electrosurgical generator comprising:
   a sensor configured to sense at least one of a tissue property or an energy property and to generate a sensor signal having an amplitude, the sensor signal being indicative of the at least one tissue property or energy property;
   a gain controller configured to reduce the amplitude of the sensor signal and to obtain a signal-to-noise ratio of the sensor signal within a predetermine range; and
   a microprocessor coupled to the generator and configured to adjust the at least one electrosurgical waveform as a function of the sensor signal.

2. The electrosurgical generator according to claim 1, wherein the gain controller includes an anti-alias filter configured to substantially block a harmonic radio frequency of the at least one electrosurgical waveform from contributing errors to processing performed by the microprocessor.

3. The electrosurgical generator according to claim 1, wherein the gain controller is further configured to process a variable DC level control signal to generate a gain control signal.

4. The electrosurgical generator according to claim 3, wherein the gain controller includes a multiplier configured to generate a multiplied signal as a function of the gain control signal.

5. The electrosurgical generator according to claim 4, wherein the gain controller further includes a summer configured to generate a difference signal as a function of the multiplied signal and the sensor signal.

6. The electrosurgical generator according to claim 4, wherein the gain controller further includes an operational amplifier configured to amplify the difference signal to normalize the sensor signal independent of the amplitude thereof.

7. The electrosurgical generator according to claim 6, wherein the gain controller further includes an input limiter to provide surge protection for the operational amplifier.

8. The electrosurgical generator according to claim 3, wherein the gain controller further includes a scaler control configured to scale the amplitude of the sensor signal and to generate a scaled sensor signal.

9. The electrosurgical generator according to claim 8, wherein the multiplier multiplies the scaled sensor signal and the gain control signal to normalize the sensor signal independent of the amplitude thereof.

10. The electrosurgical generator according to claim 1, wherein the microprocessor includes a buffer sized to store an integer multiple of a repetition rate of the sensor signal.

11. A method comprising:
   generating at least one electrosurgical waveform;
   sensing at least one energy property of the at least one electrosurgical waveform; generating a sensor signal having an amplitude, the sensor signal being indicative of the at least one energy property;
   processing the sensor signal to reduce the amplitude of the sensor signal and to obtain a signal-to-noise ratio of the sensor signal within a predetermine range; and adjusting the at least one electrosurgical waveform as a function of the sensor signal.

12. The method according to claim 11, further comprising blocking a harmonic radio frequency of the at least one electrosurgical waveform from contributing errors to processing performed by the microprocessor.

13. The method according to claim 11, further comprising processing a variable DC level control signal to generate a gain control signal.

14. The method according to claim 13, further comprising generating a multiplied signal as a function of the gain control signal.

15. The method according to claim 14, further comprising generating a difference signal as a function of the multiplied signal and the sensor signal.

16. The method according to claim 15, further comprising amplifying the difference signal to normalize the sensor signal independent of the amplitude thereof.

17. The method according to claim 13, further comprising scaling the amplitude of the sensor signal and generate a scaled sensor signal.

18. The method according to claim 17, further comprising multiplying the scaled sensor signal and the gain control signal to normalize the sensor signal independent of the amplitude thereof.

* * * * *